(12) United States Patent
Walzel et al.

(10) Patent No.: US 10,668,453 B2
(45) Date of Patent: Jun. 2, 2020

(54) COMPOSITE MATERIAL CONTAINING A BISMUTH-MOLYBDENUM-NICKEL MIXED OXIDE OR A BISMUTH-MOLYBDENUM-COBALT MIXED OXIDE AND $SIO_2$

(71) Applicant: Clariant International Ltd., Muttenz (CH)

(72) Inventors: Inga Walzel, Leipzig (DE); Gerhard Mestl, München (DE); Silvia Neumann, Grosskarolinenfeld (DE); Magdalena Pritzl, Bruckmühl (DE); Gabriele Donabauer, Bruckmühl (DE); Robert K. Grasselli, München (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 87 days.

(21) Appl. No.: 15/961,173

(22) Filed: Apr. 24, 2018

(65) Prior Publication Data

US 2019/0022629 A1 Jan. 24, 2019

Related U.S. Application Data

(62) Division of application No. 14/777,342, filed as application No. PCT/EP2014/055625 on Mar. 20, 2014, now Pat. No. 9,975,111.

(30) Foreign Application Priority Data

Mar. 20, 2013 (DE) .................. 10 2013 004 755

(51) Int. Cl.
*B01J 23/887* (2006.01)
*B01J 35/02* (2006.01)
(Continued)

(52) U.S. Cl.
CPC ........ *B01J 23/8876* (2013.01); *B01J 23/002* (2013.01); *B01J 35/023* (2013.01);
(Continued)

(58) Field of Classification Search
CPC B01J 2523/00; B01J 2523/22; B01J 2523/41; B01J 2523/54; B01J 2523/68;
(Continued)

(56) References Cited

U.S. PATENT DOCUMENTS

| 4,388,223 A * | 6/1983 | Ferlazzo ............... B01J 23/28 |
| | | 502/201 |
| 2011/0092734 A1* | 4/2011 | Hagemeyer ........... B01J 23/002 |
| | | 562/598 |

OTHER PUBLICATIONS

Evonik Industries, Inorganic Materials for Catalyst Innovation, Industry Information 2242 [2011].

* cited by examiner

*Primary Examiner* — Anthony J Zimmer

(57) ABSTRACT

The present invention relates to a process for producing a composite material and also the composite material itself. The composite material contains a bismuth-molybdenum-nickel mixed oxide or a bismuth-molybdenum-cobalt mixed oxide and a specific SiO2 as pore former. The present invention also relates to the use of the composite material according to the invention for producing a washcoat suspension and also a process for producing a coated catalyst using the composite material according to the invention. Furthermore, the present invention also relates to a coated catalyst which has a catalytically active shell comprising the composite material according to the invention on a support body. The coated catalyst according to the invention is used for preparing [alpha],[beta]-unsaturated aldehydes from olefins.

15 Claims, 9 Drawing Sheets

Figure 1:
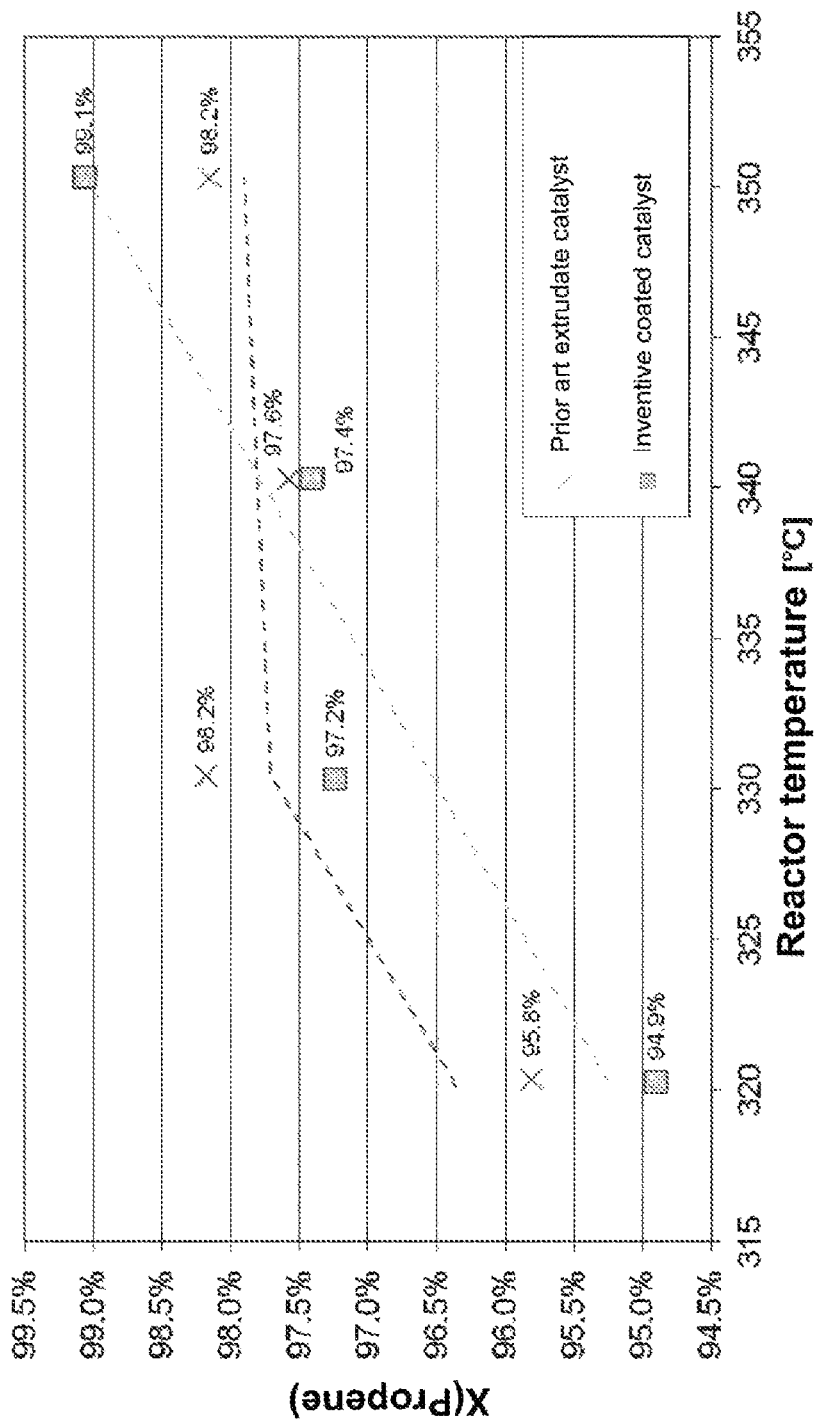

(51) Int. Cl.
  *B01J 35/10* (2006.01)
  *B01J 37/00* (2006.01)
  *B01J 37/02* (2006.01)
  *B01J 23/00* (2006.01)
  *C01G 51/00* (2006.01)
  *C01G 53/00* (2006.01)
  *C07C 45/35* (2006.01)
  *B01J 35/12* (2006.01)
  *B01J 37/08* (2006.01)
  *C07C 47/22* (2006.01)

(52) U.S. Cl.
  CPC ....... *B01J 35/1014* (2013.01); *B01J 35/1038* (2013.01); *B01J 35/12* (2013.01); *B01J 37/0009* (2013.01); *B01J 37/0045* (2013.01); *B01J 37/0215* (2013.01); *B01J 37/0221* (2013.01); *B01J 37/08* (2013.01); *C01G 51/006* (2013.01); *C01G 53/006* (2013.01); *C07C 45/35* (2013.01); *C07C 47/22* (2013.01); *B01J 37/0219* (2013.01); *B01J 2523/00* (2013.01); *C01P 2004/51* (2013.01); *C01P 2004/61* (2013.01); *C01P 2006/12* (2013.01); *C01P 2006/14* (2013.01)

(58) Field of Classification Search
  CPC ............ B01J 2523/842; B01J 2523/847; B01J 23/8876; B01J 35/12; B01J 37/0215; B01J 37/08; B01J 37/0221; B01J 35/023; B01J 35/1038; B01J 37/0009; B01J 35/1014; B01J 23/002; B01J 37/0045; B01J 37/0219; C07C 47/22; C07C 45/35; C01G 51/006; C01G 53/006
  See application file for complete search history.

COMPOSITE MATERIAL CONTAINING A BISMUTH-MOLYBDENUM-NICKEL MIXED OXIDE OR A BISMUTH-MOLYBDENUM-COBALT MIXED OXIDE AND $SiO_2$

CROSS REFERENCE TO RELATED APPLICATION

This application is a divisional application of co-pending U.S. Ser. No. 14/777,342, filed Sep. 15, 2015, by Walzel, the entire disclosure of which is hereby incorporated herein by reference.

The present invention relates to a process for producing a composite material and also to the composite material itself. The composite material contains a bismuth-molybdenum-nickel mixed oxide or a bismuth-molybdenum-cobalt mixed oxide and a specific $SiO_2$ as pore former. The present invention also relates to the use of the composite material of the invention for producing a washcoat suspension, and also to a process for producing a coated catalyst using the composite material of the invention. Furthermore, the present invention also relates to a coated catalyst which has a catalytically active shell, comprising the composite material of the invention, on a support body. The coated catalyst of the invention is used for preparing $\alpha,\beta$-unsaturated aldehydes from olefins.

Molybdenum-containing mixed oxides have been used to date in the prior art as catalysts for the preparation of acrylonitrile from propene by ammoxidation or for the preparation of $\alpha,\beta$-unsaturated aldehydes from olefins. In these contexts, these molybdenum mixed oxides are obtained customarily by precipitation techniques, sol-gel methods, or solid-state reactions. Also known in the prior art is the possibility of preparing molybdenum mixed oxides by spraying a solution of starting materials into a pulsation reactor, with a small particle size and a very large BET surface area.

Although in particular the molybdenum mixed oxides with small particle size and very large BET surface area are exceptionally suitable for the production of catalysts, there is still a need for the stated catalysts to be improved in terms of their activity and selectivity. At the same time, there is also a need to minimize the amount of the relatively expensive starting substances in the production of such catalysts, and nevertheless to provide a catalyst featuring high performance.

It was an object of the present invention, therefore, to provide a composite material as active composition for a catalyst, featuring high catalytic performance. Moreover, a further object of the present invention was to provide a process for producing a composite material and a catalyst that allows the amount of active metals used to be minimized without any loss of catalytic performance by the catalyst in comparison to catalysts of the prior art.

In achievement of the stated objects, the present invention provides a process for producing a composite material, which comprises the following steps:
(a) preparing a first aqueous solution containing salts of bismuth and of nickel or salts of bismuth and of cobalt, preferably salts of bismuth and of nickel;
(b) preparing a second aqueous solution containing a molybdenum compound and optionally a binder;
(c) adding the first aqueous solution to the second aqueous solution, forming a first suspension;
(d) adding a second suspension to the first suspension, the second suspension containing $SiO_2$ which has a pore volume in the range from 0.1 to 10 ml/g and an average particle size in the range from 3 to 20 µm; and
(e) spray-calcining the third suspension at a temperature in the range from 200 to 600° C., to give the composite material containing a bismuth-molybdenum-nickel mixed oxide or a bismuth-molybdenum-cobalt mixed oxide, preferably a bismuth-molybdenum-nickel mixed oxide.

The terms "bismuth-molybdenum-cobalt mixed oxide" and "bismuth-molybdenum-nickel mixed oxide" are to be interpreted in the present specification as referring to a mixed oxide which comprises, as oxidic metals, bismuth, molybdenum and cobalt or bismuth, molybdenum and nickel, respectively.

In a further-preferred embodiment, the first aqueous solution in step (a) may further contain a salt of magnesium or a salt of iron, or both of these salts.

In an even further-preferred embodiment, the first aqueous solution may contain a potassium compound. In an even further embodiment, the first aqueous solution may contain not only a potassium compound but also a cesium compound, or a compound containing potassium and cesium.

The first aqueous solution is preferably prepared by dissolving the metal salts used therein at a temperature in the range from 40 to 60° C., preferably with stirring, in a very small amount of deionized water.

In a further-preferred embodiment, the first aqueous solution is prepared by initially introducing water with stirring at a temperature in the range from 40 to 60° C., and adding first the nickel salt and then the bismuth salt. If the first aqueous solution is to include a potassium compound, the sequence of addition is preferably as follows: addition of the nickel salt, addition of the potassium compound, and subsequently addition of the bismuth salt. Where an iron salt as well is used in the preparation of the first aqueous solution, the iron salt is added preferably before the nickel salt is added. Where a magnesium salt as well is used for the first aqueous solution, the addition of the magnesium salt is made preferably after the addition of the nickel salt but before the addition of the potassium compound and/or before the addition of the bismuth compound.

It is particularly preferable for the iron, nickel and/or magnesium salts used to comprise water-soluble salts of these metals. Employed with more particular preference are the nitrates of these metal salts. In one especially preferred embodiment of the present invention, the first aqueous solution is prepared using metal nitrate hydrates. An iron salt used is preferably iron nitrate nonahydrate; a nickel salt used is preferably nickel nitrate hexahydrate; and a magnesium salt used is preferably magnesium nitrate hexahydrate. Alternatively or additionally to the use of a nickel salt, the first aqueous solution may also be prepared using a cobalt salt, preferably a water-soluble cobalt salt such as cobalt nitrate hexahydrate. In terms of the sequence of addition of the components, the cobalt salt is added at the same point as the nickel salt.

The bismuth salt is preferably one which undergoes liquefaction on heating to 60° C. The reason for using a bismuth salt which melts at a temperature between 40 and 60° C. is that in general bismuth compounds are poorly soluble in water, and can be brought into solution only by strong acidification. Consequently it is especially preferred in accordance with the invention for a hydrate salt of the bismuth to be used for preparing the first aqueous solution, this salt being present in the form of a so-called aqueous melt by virtue of its high content of water of hydration, at temperatures between 40 and 60° C. In the present invention as well, therefore, the preference is for all metal salts used for preparing the first aqueous solution to be hydrate salts of these compounds. In this way, it is not automatically necessary to introduce water initially for dissolution in preparing the first aqueous solution; instead, the hydrate metal salts used can be liquefied in succession with stirring at a temperature between 40 and 60° C. to form an aqueous melt. Any bismuth salt used can also be further-processed in this way. For complete dissolution, it is also possible, optionally, to carry out acidification, preferably with nitric acid. In the prior art, in the preparation of solutions containing bismuth, it was always necessary to use a superstoichiometric amount of bismuth in order to have the desired amount of bismuth present.

Potassium compound used in accordance with the invention may comprise all water-soluble potassium compounds or potassium salts. It is nevertheless preferred, in accordance with the invention, for potassium nitrate or potassium hydroxide, more preferably potassium hydroxide, to be used as potassium compound.

The amount of the bismuth salt in the first solution is preferably in the range from 3 to 9 wt %, more preferably in the range from 4 to 8 wt %, and most preferably in the range from 5 to 7 wt %, based on the total weight of the first solution including water.

The amount of the nickel salt or of the cobalt salt, or their total, in the first solution is preferably in the range from 35 to 60 wt %, more preferably in the range from 40 to 55 wt %, and most preferably in the range from 45 to 50 wt %, based on the total weight of the first solution including water.

The amount of the iron salt in the first solution is preferably in the range from 0 to 40 wt %, more preferably in the range from 1 to 35 wt %, even more preferably in the range from 5 to 30 wt %, and most preferably in the range from 15 to 25 wt %, based on the total weight of the first solution including water.

Where the first solution includes an iron salt, the process of the invention sees formation of a mixed oxide which also contains iron in the form of iron oxide.

The amount of the magnesium salt in the first solution is preferably in the range from 0 to 25 wt %, more preferably in the range from 1 to 20 wt %, even more preferably in the range from 5 to 17 wt %, and most preferably in the range from 10 to 14 wt %, based on the total weight of the first solution including water. Where the first solution includes a magnesium salt, the process of the invention sees formation of a mixed oxide which also contains magnesium in the form of magnesium oxide.

The amount of the potassium compound in the first solution is preferably in the range from 0 to 0.1 wt %, more preferably in the range from 0.005 to 0.08 wt %, even more preferably in the range from 0.02 to 0.06, and most preferably in the range from 0.03 to 0.05 wt %, based on the total weight of the first solution including water.

In step (b) of the process of the invention, the second aqueous solution, containing a molybdenum compound and optionally a binder, is prepared by initially introducing the preferably water-soluble molybdenum compound and then dissolving it in water. Where, additionally, a binder is used, the molybdenum compound is introduced first of all and then the binder, followed by dissolution in water.

Molybdenum compound used may be any conceivable water-soluble molybdenum compound, though it is preferred for the molybdenum compound to be a molybdate. With particular preference, the molybdenum compound is a heptamolybdate, more preferably an ammonium hepta-molybdate, and most preferably ammonium heptamolybdate tetrahydrate.

The binder used optionally in preparing the second aqueous solution is preferably an $SiO_2$-containing binder. This binder preferably has a sodium content of less than 400 ppm, more preferably less than 300 ppm, and most preferably less than 250 ppm. Where the binder is an $SiO_2$-containing binder, the $SiO_2$ preferably has a BET surface area of in the range from 140 to 220 $m^2/g$, more preferably 160 to 200 $m^2/g$, and most preferably 180 to 190 $m^2/g$. The density of the $SiO_2$ here is preferably in the range from 1.00 to 1.40 $g/cm^3$, more preferably 1.15 to 1.30 $g/cm^3$, and most preferably in the range from 1.20 to 1.25 $g/cm^3$.

The amount of the molybdenum compound in the second solution is preferably in the range from 5 to 40 wt %, more preferably in the range from 10 to 35 wt %, and most preferably in the range from 18 to 26 wt %, based on the total weight of the second solution including water.

The amount of the binder in the second solution is preferably in the range from 0 to 20 wt %, more preferably in the range from 1 to 17 wt %, even more preferably in the range from 4 to 13, and most preferably in the range from 6 to 11 wt %, based on the total weight of the second solution including water.

It is further preferred for the addition of the first aqueous solution to the second aqueous solution in step (c) of the process of the invention to be carried out such that the second aqueous solution is stirred rapidly with the aid of a stirring mechanism, and the first aqueous solution is added slowly, dropwise or by pumping, to the second aqueous solution. In this procedure, a precipitate is formed, thereby forming a first suspension in step (c).

Furthermore, a second suspension is prepared, separately from the first suspension formed, and contains an $SiO_2$ in water, having a pore volume in the range from 0.1 to 10 ml/g, more preferably 0.5 to 5 ml/g, and most preferably 1 to 3 ml/g, and having an average particle size in the range from 3 to 20 μm, more preferably 5 to 15 μm, and most preferably 8 to 11 μm. It is further preferred for the $SiO_2$ used for preparing the second suspension to have an oil absorption in the range from 250 g/100 g to 400 g/100 g, more preferably 300 g/100 g to 350 g/100 g.

The amount of $SiO_2$ in the second suspension is in the range from 1 to 20 wt %, more preferably in the range from 2 to 10 wt %, and most preferably in the range from 3 to 7 wt %, based on the total weight of the suspension including water.

In step (d) of the process of the invention, the second suspension is added to the first suspension, preferably with stirring of the latter.

In the process of the invention, the amount of second suspension is preferably selected such that the weight ratio of the molybdenum compound used in the first suspension to the $SiO_2$ of the second suspension is in the range from 5 to 25, more preferably in the range from 10 to 20, and most preferably in the range from 12 to 16.

Similarly, the weight ratio of the nickel or cobalt salt used in the first suspension to the $SiO_2$ in the second suspension is in the range from 5 to 25, more preferably in the range from 10 to 20, and most preferably in the range from 11 to 15.

Further to the addition of the second suspension to the first suspension, it is also possible in step (d) for a precipitant to be added to the first suspension. The precipitant is preferably a cationic polymer, a cationic polyacrylamide derivative being preferred. The amount of precipitant to be added is preferably selected such that the weight ratio of molybdenum compound to precipitant is in the range from $1.3 \times 10^2$ to $1.3 \times 10^4$, more preferably in the range from $0.3 \times 10^3$ to $0.3 \times 10^4$, and most preferably in the range from $1.1 \times 10^3$ to $1.7 \times 10^3$.

The combining of the first and second suspensions in step (d) of the process of the invention produces a third suspension, which, in the subsequent step (e) of the process of the invention, is spray-calcined at a temperature in the range from 200 to 600° C., more preferably 300 to 550° C., and more preferably 450 to 520° C. This produces a composite material which contains a bismuth-molybdenum-nickel mixed oxide or a bismuth-molybdenum-cobalt mixed oxide.

In the context of the invention, the term "spray-calcining" means that the suspension is sprayed into a calcining reactor or calcining oven which is preheated within the specified temperature range. In this way, the liquid evaporates and the composite material is formed. With particular preference, the calcining ovens or calcining reactors used are those as employed for the preparation of mixed oxides in the specification having the publication number DE 10 2008 017 311 for example.

After the spray-calcining, it is also possible, optionally, for further calcining to be carried out in a calcining oven at a temperature in the range from 250 to 450° C., more preferably in the range from 300 to 400° C.

The present invention also relates to a composite material which contains a bismuth-molybdenum-nickel mixed oxide or a bismuth-molybdenum-cobalt mixed oxide and $SiO_2$, the $SiO_2$ having a pore volume in the range from 0.1 to 10 ml/g and an average particle size in the range from 3 to 20 μm. The preferred parameter ranges stated earlier on above, in connection with the process of the invention in step (d), for the $SiO_2$ used in the second suspension are also preferred for the $SiO_2$ present in the composite material of the invention. In other words, the $SiO_2$ present in the composite material is the $SiO_2$ which was used in the second suspension in the process of the invention.

Accordingly, the present invention also relates to a composite material which has been produced by the process of the invention.

The use of the $SiO_2$ in the process of the invention in step (d), or the presence of the $SiO_2$ with the stated pore volume and the stated average particle size, has the advantage that the composite material has a defined pore volume, which is important for the high activity and selectivity of the catalyst produced therefrom.

The BET surface area of the composite material of the invention is preferably in the range from 20 to 60 m²/g, more preferably in the range from 30 to 50 m²/g, and most preferably in the range from 35 to 45 m²/g.

The pore volume of the composite material of the invention is preferably in the range from 0.08 to 0.24 cm³/g and even more preferably in the range from 0.12 to 0.20 cm³/g.

90% of all the particles of the composite material of the invention ($d_{90}$) preferably have a particle size of less than 125 μm. 50% of all the particles of the composite material of the invention ($d_{50}$) preferably have a particle size of less than 50 μm, whereas 10% of all the particles ($d_{10}$) preferably have a particle size of less than 7 μm.

The present invention also relates to the use of the composite material of the invention for producing a washcoat suspension.

In other words, the present invention also relates to a washcoat suspension which contains the composite material of the invention.

To produce the washcoat suspension of the invention, composite material of the invention is slurried in deionized water. The washcoat suspension thus produced is subsequently subjected preferably to Ultraturrax treatment, in order to ensure that the particle size of the particles of composite material is in the range from 1 to 100 μm. Subsequently, as and when required, an inorganic and/or organic pore former, a binder, and an adhesive may be added. Where these further components are used, it is also possible, alternatively, for the grinding with the Ultraturrax to take place after the addition of these components.

The amount of the composite material in the washcoat suspension of the invention is preferably in the range from 1 to 50 wt %, more preferably in the range from 5 to 40 wt %, and most preferably in the range from 10 to 35 wt %, based on the total weight of the washcoat suspension.

Binder used for producing the washcoat suspension may be the same binder as in the composite material production process. The amount of the binder in the washcoat suspension of the invention is preferably in the range from 1 to 15 wt %, more preferably in the range from 3 to 12 wt %, and most preferably in the range from 5 to 10 wt %, based on the total weight of the washcoat suspension.

As inorganic pore former, it is preferred for an $SiO_2$ to be used that has the same properties as the $SiO_2$ employed in the second aqueous suspension in step (d) of the process of the invention for producing the composite material. The amount of inorganic pore former in the washcoat suspension of the invention is preferably in the range from 0.1 to 3 wt %, more preferably in the range from 0.5 to 2 wt %, and most preferably in the range from 0.6 to 1 wt %, based on the total weight of the washcoat suspension.

Organic pore former used may be any organic pore former having a high carbon content. As organic pore former it is possible accordingly to use coconut shell flour for example. The amount of organic pore former in the washcoat suspension of the invention is preferably in the range from 0.5 to 10 wt %, more preferably in the range from 1 to 5 wt %, and most preferably in the range from 2 to 3 wt %, based on the total weight of the washcoat suspension.

Adhesive used preferably comprises inorganic adhesion promoters, such as silanes. The silanes are preferably alkylalkoxysilanes, such as N-(2-aminoethyl)-3-aminopropylmethyldimethoxysilane, for example. The amount of the adhesive in the washcoat suspension of the invention is preferably in the range from 0.1 to 3 wt %, more preferably in the range from 0.2 to 2 wt %, and most preferably in the range from 0.3 to 1 wt %, based on the total weight of the washcoat suspension.

The Ultraturrax treatment takes place preferably in the range from 1 to 5 minutes at preferably 6000 to 12 000 rpm.

In the washcoat suspension of the invention it is also possible, optionally, for an alkali metal compound to be used, more particularly a potassium or cesium compound, such as potassium hydroxide, cesium hydroxide, potassium nitrate or cesium nitrate. The total amount of the alkali metal/metals in the washcoat suspension of the invention in this case is preferably in the range from 0.05 to 0.1 wt., based on the total weight of the washcoat suspension. Further preference is given to using both potassium and cesium as alkali metal. In this case it is preferred for the atomic ratio of potassium to cesium to be in the range from 1 to 10, more preferably in the range from 2 to 8, and most preferably in the range from 3 to 6.

The present invention also relates to a process for producing a coated catalyst, which comprises the following steps:

(a) producing an aqueous suspension of the composite material in accordance with the production of the washcoat suspension of the invention;
(b) coating support bodies with the aqueous suspension produced in step (a); and
(c) calcining the coated support bodies at a temperature in the range from 500 to 700° C., more preferably at 550 to 650° C., even more preferably 590 to 620° C., and most preferably about 610° C.

The calcining in step (c) of the process of the invention is carried out preferably over a duration in the range from 1 to 5 h, more preferably 2 to 4 h, and most preferably about 3 h.

In accordance with the invention it is preferred for the coating of the support body to be carried out in such a way that the aqueous suspension produced in step (a) is sprayed onto a bed of support bodies that is subject to a circulatory motion.

The term "coated catalyst" refers to a catalyst comprising a support body coated with a shell of catalytically active material. The surface of the support body bears an additional applied coat, in which there is a catalytically active material. This coat therefore forms an additional layer of material, constructed as a shell around the support body; in other words, the support material itself does not form part of the shell, but the shell is formed by the catalytically active material itself or by a matrix material which comprises a catalytically active material.

The support body is preferably made of an inert material. It may be porous or nonporous. Preferably, however, the support body is nonporous. The support body consists preferably of particles having a regular or irregular shape, such as, for example, spheres, tablets, cylinders, solid cylinders or hollow cylinders, rings, stars, or other shapes, and in its dimensions—such as diameter, length or width, for example—exhibits a range of 1 to 10 mm, preferably 3 to 9 mm. Spherical particles, in other words, for example, ball-shaped particles having a diameter of 3 to 8 mm are preferred in accordance with the invention.

The support body material may comprise any nonporous or porous substance, preferably nonporous substance. Examples of materials for this are titanium oxide, silicon oxide, aluminum oxide, zirconium oxide, magnesium oxide, silicon carbide, magnesium silicate, zinc oxide, zeolites, phyllosilicates, and nanomaterials, such as carbon nanotubes or carbon nanofibers, for example, or ceramics such as steatite, for example. A preferred support material is steatite, more preferably steatite beads.

It is particularly preferred for the support bodies, during the (sprayed) application of the suspension containing the composite material, to be subjected to a circulatory motion, allowing the support body to be sprayed uniformly from all sides. The circulatory motion may be accomplished in principle by any known mechanical stirring apparatus, such as a film coating drum, for example. It is nevertheless preferred in accordance with the invention for the circulatory motion of the support bodies to be carried out by means of a process gas, in, for example, a fluidized bed, an eddy layer, or in a coating chamber of an Innojet Aircoater. Here, the support bodies are moved by the inwardly blown process gas. The process gas here is preferably guided such that the support bodies are held in a controlled sliding layer of the process. The process gas here is preferably heated, causing rapid evaporation of the solvent. In this way, the precursor compounds are present in the stated defined shell of the support body. The spraying rate during sprayed application is preferably selected such that an equilibrium is reached between the evaporation rate of the solvent and the feed rate of the precursor compounds on the support body. This allows the desired shell thickness to be brought about in the shell. Depending on the spraying rate, accordingly, the shell thickness can be infinitely adjusted and optimized, to a thickness of 2 mm, for example. However, very thin shells as well are possible in this way, with a thickness of less than 200 μm.

It is particularly preferred for the spraying rate during the sprayed application of the washcoat suspension to be constant and to be situated in the range of a suspension mass flow rate of 0.5 to 6 g/min per 100 g of shaped support body for coating, more preferably in the range from 1 to 4 g/min per 100 g of support body for coating, even more preferably from 1 to 3 g/min per 100 g of support body for coating. In other words, the ratio of the weight of the spray-applied suspension to the weight of the bed of support body is in the range from 0.005 to 0.06, more preferably 0.01 to 0.04, and even more preferably 0.01 to 0.03. A mass flow ratio above the stated range results in considerable spray losses during catalyst production and hence in considerable financial loss; a mass flow rate or ratio below the stated range, however, leads to a very long duration during catalyst production and so makes production inefficient.

Where a fluidized bed unit is used, it is preferred for the support bodies to circulate elliptically or torroidally in the fluidized bed. In order to give an idea of how the support bodies move in such fluidized beds, it may be noted that in the case of "elliptical revolution", the support bodies in the fluidized bed move in a vertical plane on an elliptical path, with fluctuation in the size of the main and secondary axes. In the case of "toroidal revolution", the support bodies in the fluidized bed move in a vertical plane on an elliptical path with fluctuating sizes of the main and secondary axes, and in a horizontal plane on a circular path with a fluctuating size of the radius. On average, the support bodies move on an elliptical path in a vertical plane in the case of "elliptical revolution", and on a toroidal path in the case of "toroidal revolution", meaning that a support body helically descends the surface of a torus with vertically elliptical section.

Furthermore, the support body that is used in the process of the invention for producing the coated catalyst is heated during spraying, by means of heated process gas, for example. The process gas here preferably has a temperature of 30 to 120° C., more preferably 40 to 110° C., and most preferably 50 to 100° C. The stated upper limits ought to be observed in order to ensure that the stated outer shell has a low layer thickness.

Process gas used is preferably air, although use may also be made of inert gases such as, for example, nitrogen, $CO_2$, helium, neon, argon and mixtures thereof.

The sprayed application of the washcoat suspension in the process of the invention is accomplished preferably by atomizing the suspension using a spraying nozzle. In this case, preferably, an annular gap nozzle is used, emitting a spray cloud whose plane of symmetry runs preferably parallel to the plane of the apparatus base. As a result of the 360° extent of the spray cloud, the support bodies which drop down centrally can be sprayed with the solution with particular uniformity. In this case the annular gap nozzle, i.e. its opening, is embedded preferably completely in the unit that implements the circulatory movement of the support bodies.

As a result of the step (c) of catalyst production, the coated catalyst is activated, more preferably at about 610° C. for about 3 hours in air. Thereafter the catalyst can be used.

The present invention also relates to a coated catalyst which comprises a support and a catalytically active shell thereon, wherein the catalytically active shell contains a bismuth-molybdenum-nickel mixed oxide or a bismuth-molybdenum-cobalt mixed oxide, and $SiO_2$, the $SiO_2$ having a pore volume in the range from 0.1 to 10 ml/g and an average particle size in the 3 to 20 μm range. The preferred parameters of the $SiO_2$ used in step (d) of the process for producing the composite material, as stated in connection with that process, are preferred here as well. The coated catalyst of the invention is preferably one which has been produced by and/or is obtainable by the process of the invention for producing a coated catalyst.

It is preferred for the fraction of the catalytically active shell to be in the range from 15 to 45 wt %, more preferably 20 to 40 wt % in the case of the coated catalyst of the invention, based on the total weight of the coated catalyst.

The thickness of the shell of the coated catalyst of the invention is preferably in the range from 100 to 1500 μm, more preferably from 300 to 1000 μm, and even more preferably 500 to 900 μm. It is preferred, moreover, for the porosity of the catalytically active shell of the coated catalyst of the invention to be greater than 40%, more preferably greater than 50%. Furthermore, the pore volume of the catalytically active shell is preferably 0.45 to 0.75 $m^3/g$, more preferably 0.5 to 0.7 $m^3/g$, and most preferably 0.55 to 0.67 $m^3/g$. The average pore radius in the shell of the coated catalyst is in the range from 150 to 210 nm, more preferably 160 to 200 nm, and most preferably 170 to 190 nm. The relevant determinations were made in accordance with DIN 66133 (Hg porosimetry). BET surface area of the coated catalyst of the invention is preferably in the range from 10 to 60 $m^2/g$, more preferably 20 to 50 $m^2/g$, and most preferably in the range from 20 to 40 $m^2/g$. The BET surface area is determined by the 1-point method, by nitrogen absorption, in accordance with DIN 66132.

A further embodiment of the present invention also relates to the use of the coated catalyst of the invention, and/or of a coated catalyst produced by the steps of the process of the invention for producing a coated catalyst, for preparing α,β-unsaturated aldehydes from olefins, more particularly the preparation of acrolein from propene.

In other words, therefore, the present invention also relates to a process for preparing α,β-unsaturated aldehydes from olefins, or acrolein from propene, using a coated catalyst of the invention.

The above invention is now to be elucidated in more detail with reference to figures and examples, which, however, are not to be interpreted as imposing any restriction on the scope of protection of the claims.

FIGURES

FIG. 1: FIG. 1 shows, in a diagram, the conversion of propene as a function of the reactor temperature, using an inventive coated catalyst as per example 3 and using a solid extrudate catalyst as per comparative example 1.

Figure 2:
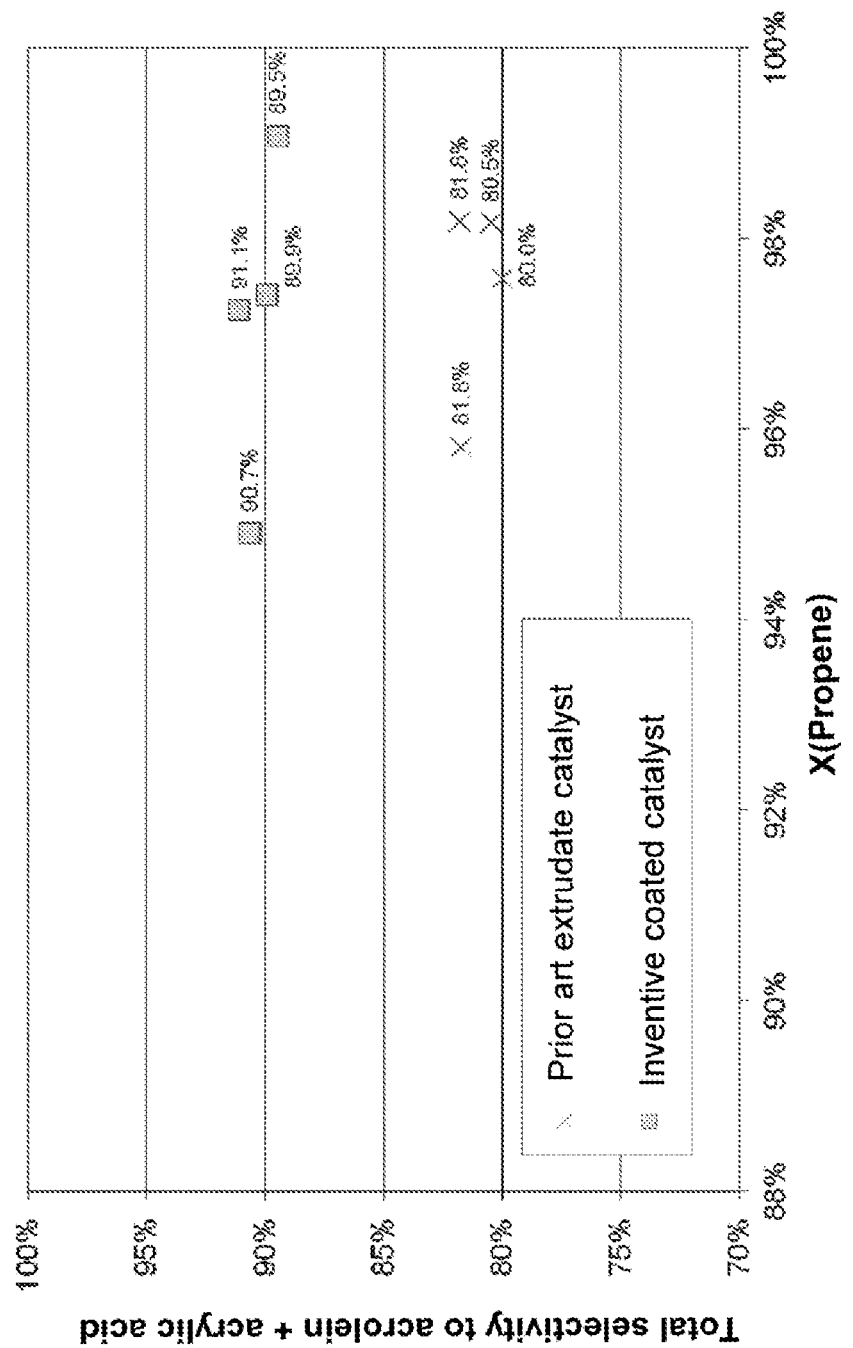

FIG. 2: FIG. 2 shows the sum of selectivity to acrolein and acrylic acid as a function of the amount of converted propene for an inventive coated catalyst as per example 3 and a solid extrudate catalyst as per comparative example 1.

Figure 3:
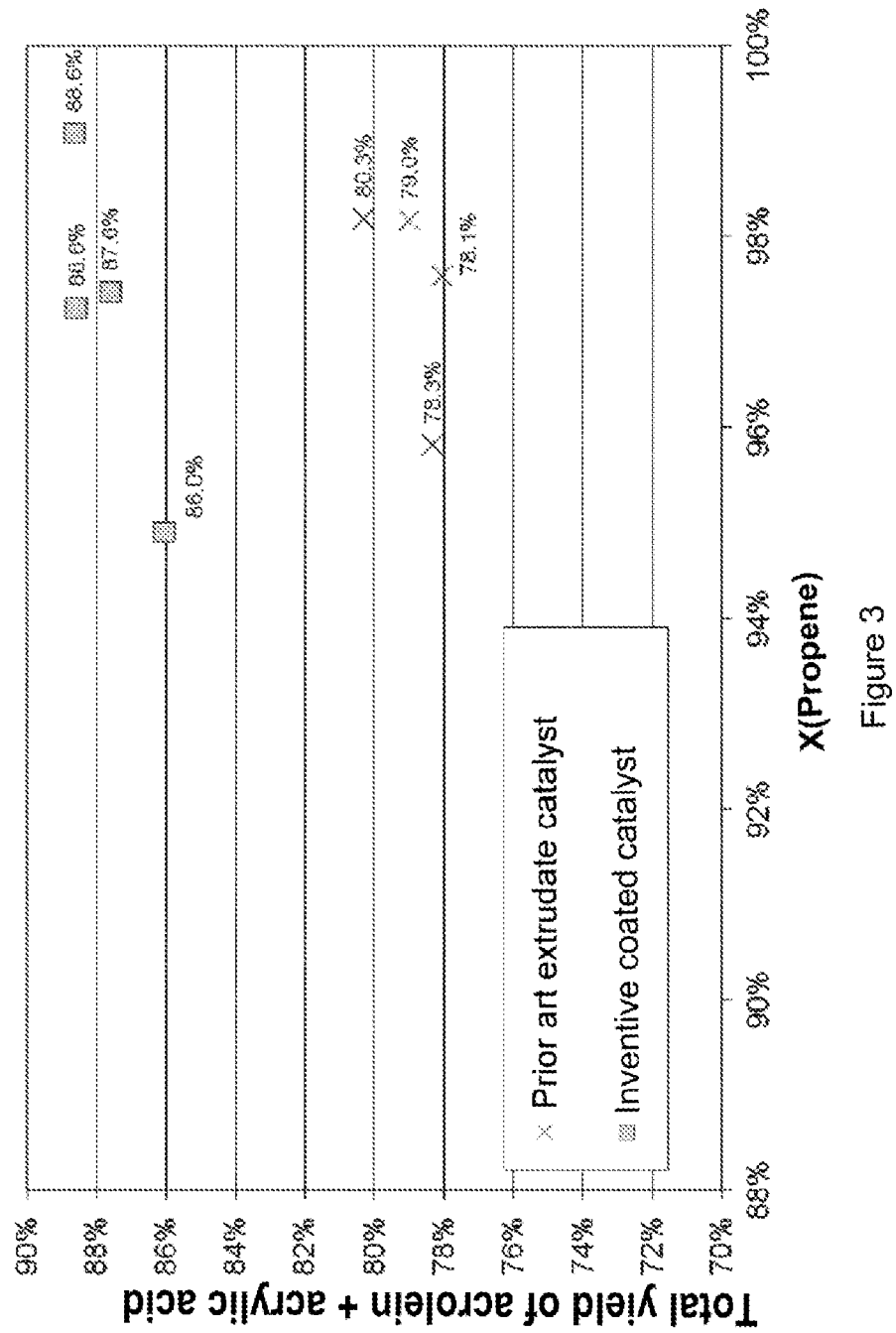

FIG. 3: FIG. 3 shows the sum of yield of acrolein and acrylic acid as a function of the amount of consumed propene for an inventive coated catalyst as per example 3 and a solid extrudate catalyst as per comparative example 1.

Figure 4:
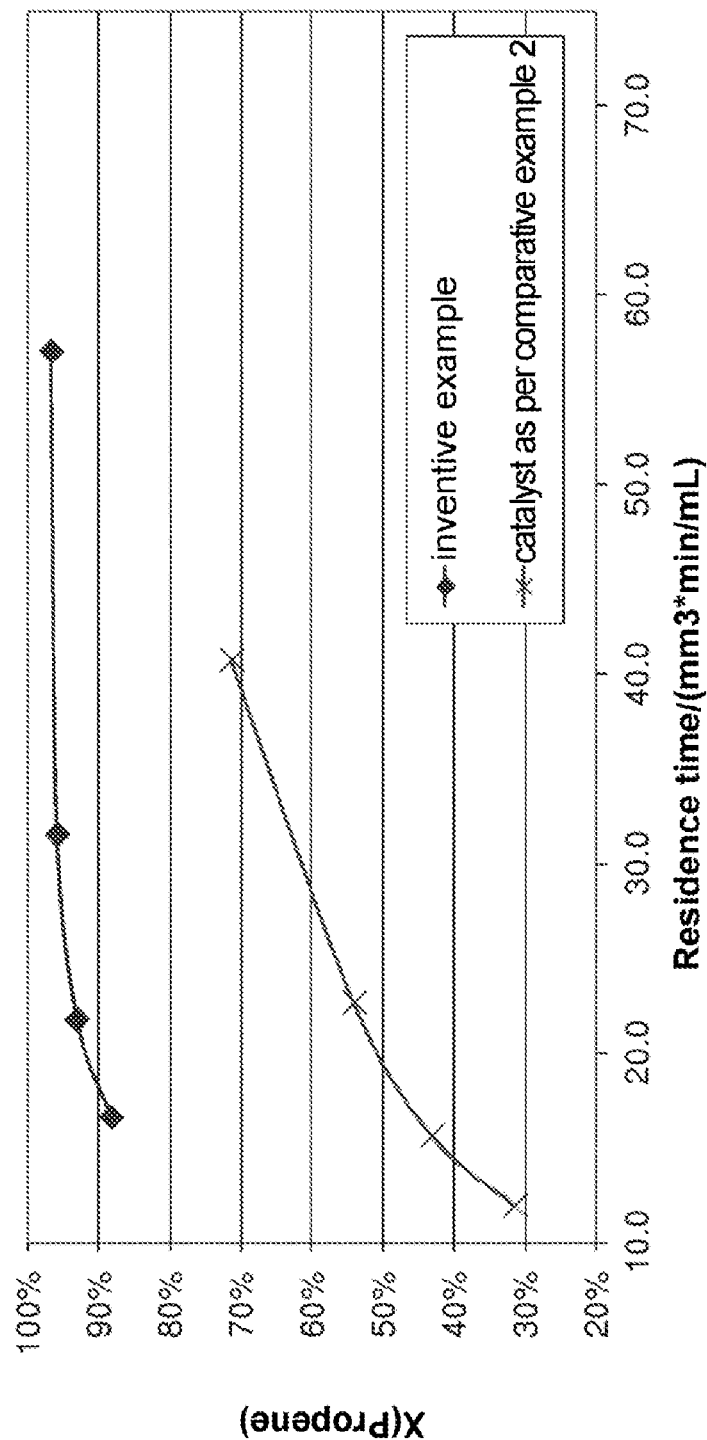

FIG. 4: FIG. 4 shows, in a diagram, the conversion of propene as a function of the reactor residence time, using an inventive coated catalyst as per example 3 and using a coated catalyst as per comparative example 2.

Figure 5:
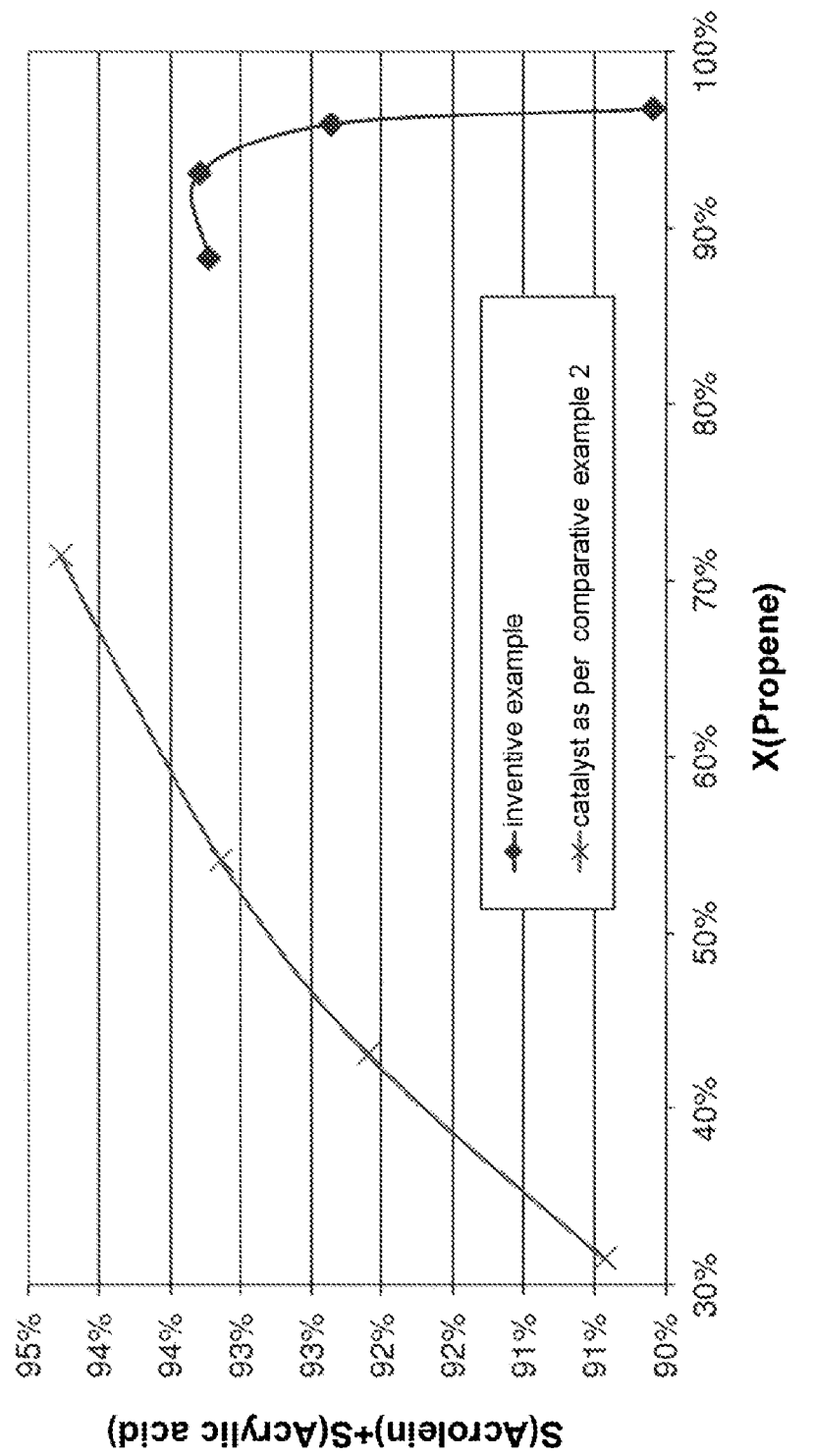

FIG. 5: FIG. 5 shows the sum of yield of acrolein and acrylic acid as a function of the amount of consumed propene for an inventive coated catalyst as per example 3 and a coated catalyst as per comparative example 2.

Figure 6:
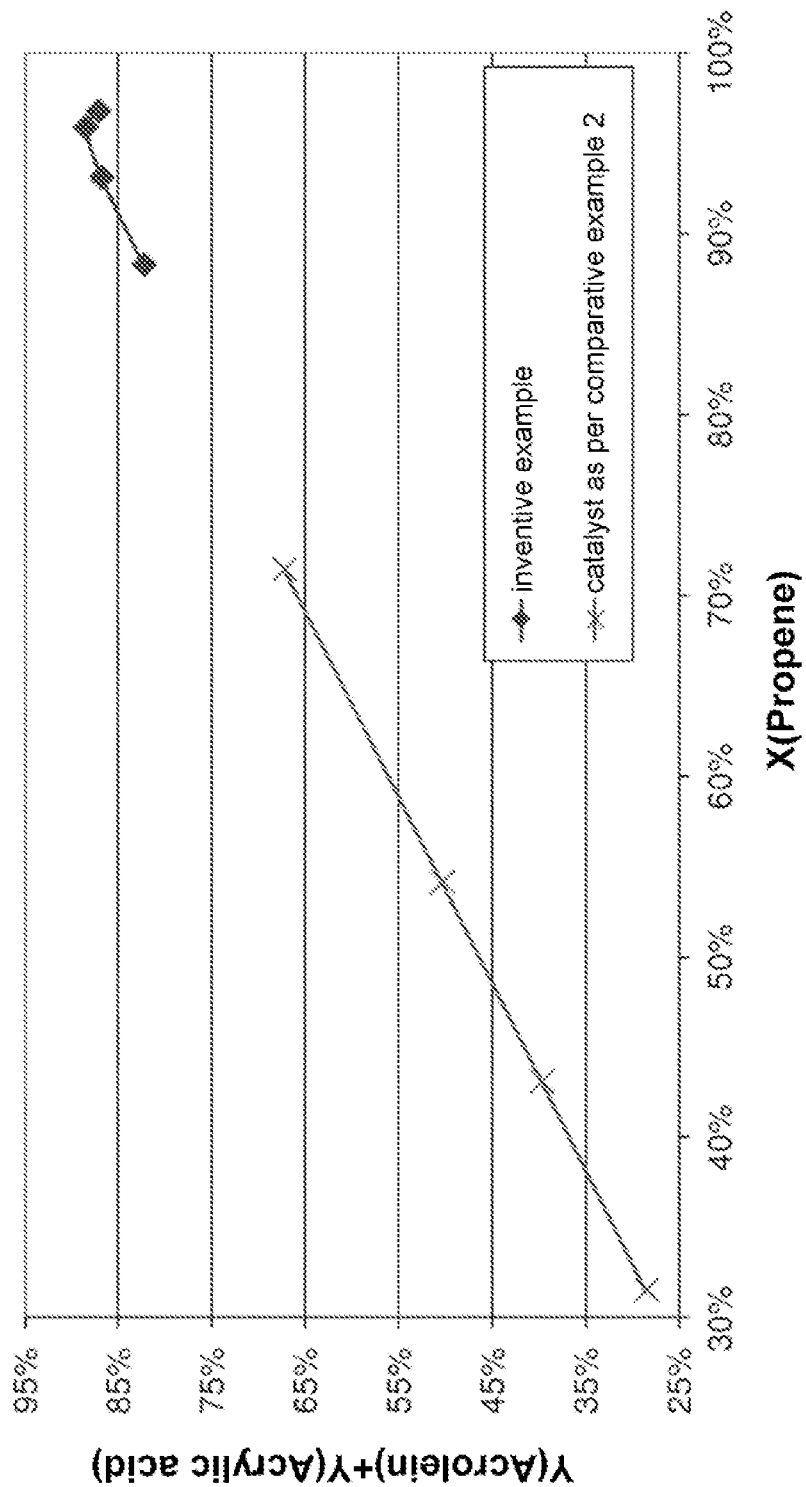

FIG. 6: FIG. 6 shows the sum of selectivity to acrolein and acrylic acid as a function of the amount of converted propene for an inventive coated catalyst as per example 3 and a coated catalyst as per comparative example 2.

Figure 7:
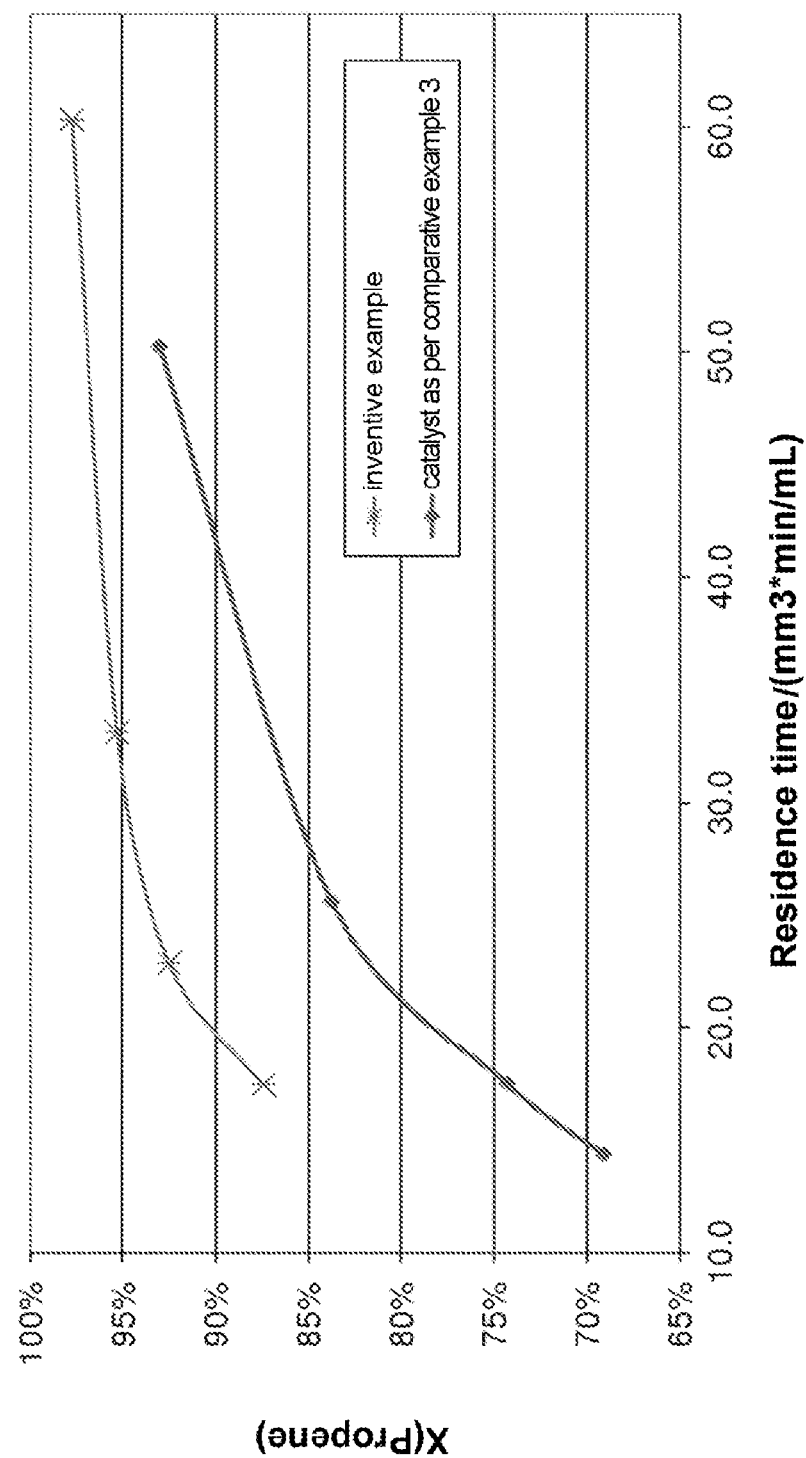

FIG. 7: FIG. 7 shows, in a diagram, the conversion of propene as a function of the reactor residence time, using an inventive coated catalyst as per example 3 and using a coated catalyst as per comparative example 3.

Figure 8:
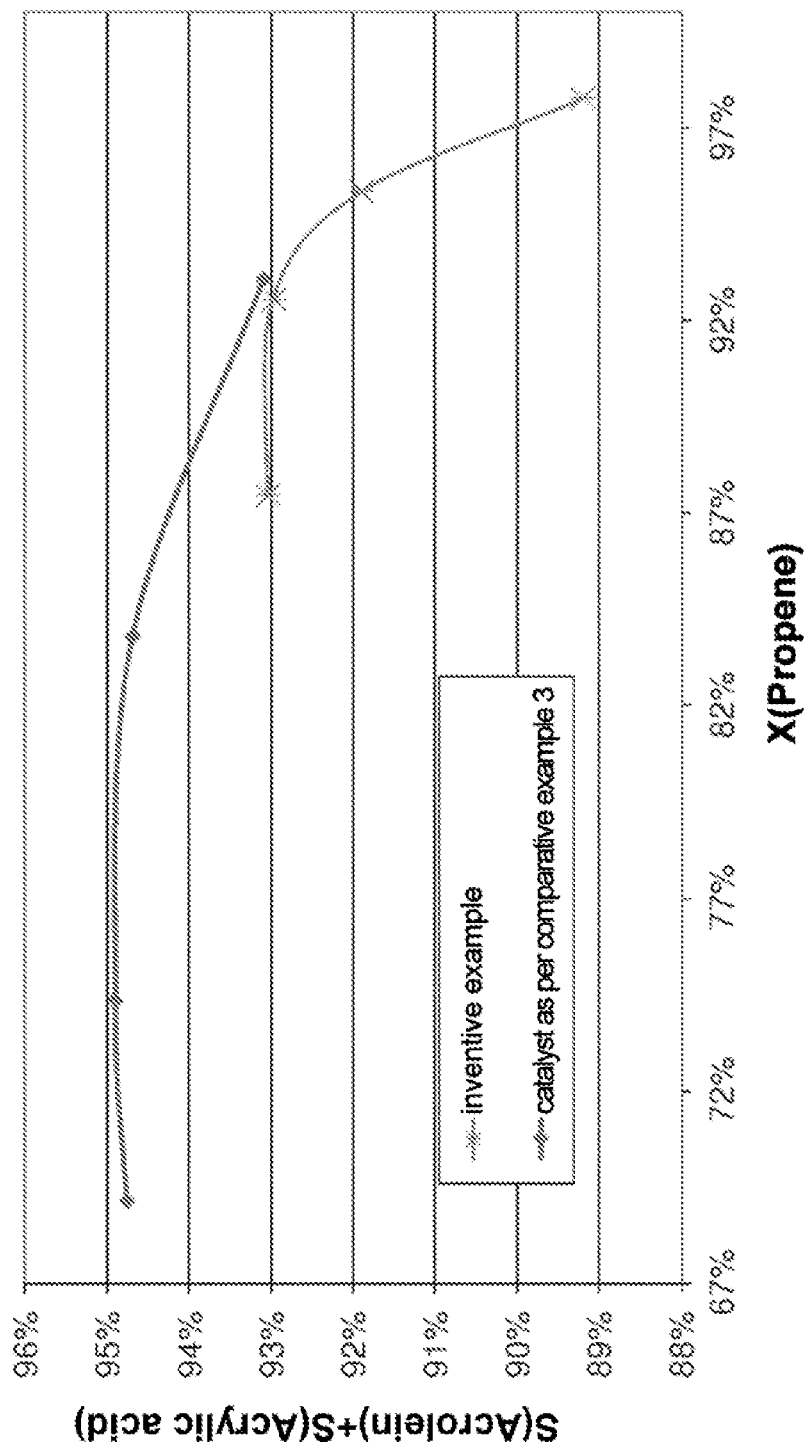

FIG. 8: FIG. 8 shows the sum of selectivity to acrolein and acrylic acid as a function of the amount of converted propene for an inventive coated catalyst as per example 3 and a catalyst as per comparative example 3.

Figure 9:
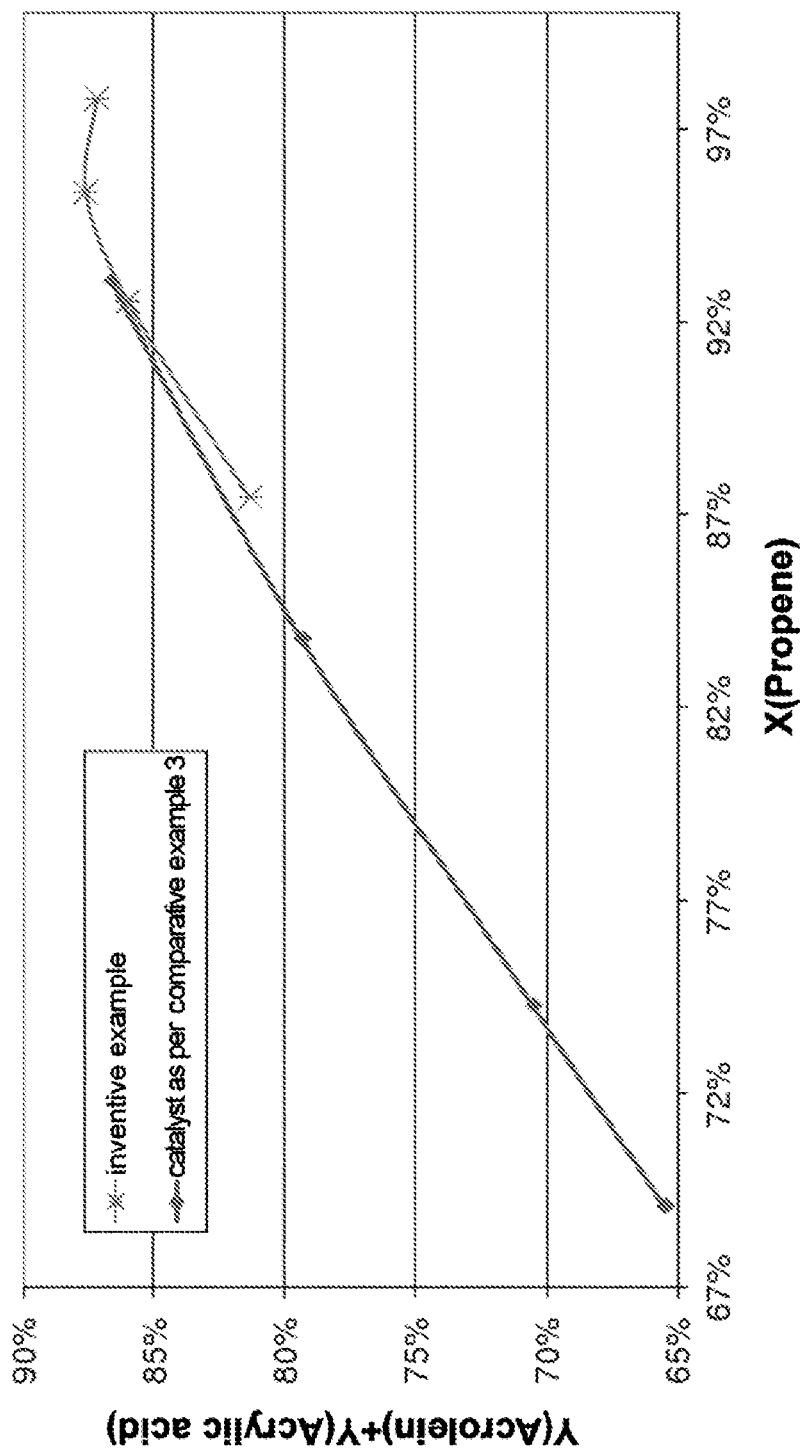

FIG. 9: FIG. 9 shows the sum of yield of acrolein and acrylic acid as a function of the amount of consumed propene for an inventive coated catalyst as per example 3 and a catalyst as per comparative example 3.

EXAMPLES

Example 1

Production of an Inventive Composite Material

A 5 liter glass beaker is charged with 0.727 kg of distilled water, which is heated to 60° C. Then 1.02 kg of iron nitrate nonahydrate (Honeywell; batch: B1960) are added. Without further heating, 2.37 kg of nickel nitrate hexahydrate (ALFA Aesar; batch: 61101000) and 0.62 kg of magnesium nitrate hexahydrate (Honeywell; batch: 90140) are then added, and the mixture is stirred until this has likewise dissolved. Following renewed heating to 50° C., 0.039 kg of 1M KOH (Merck; batch: HC111978) is added. Following the addition of the potassium hydroxide, a brown precipitate can be seen, but quickly dissolves again. Then 0.3 kg of bismuth nitrate pentahydrate (ALFA Aesar; batch: 42060004) is added. The solution is stirred at 35° C. for about 12 hours.

In a further batch, 8.3 kg of distilled water are initially introduced. Then 2.62 kg of ammonium heptamolybdate tetrahydrate (HC Starck; batch: 1163/048) are added to the solution and dissolved with stirring at 35° C. 1.1 kg of Bindzil 2034Di (Akzo Nobel; batch: N00210) are added thereto. Measurement of the pH at a temperature of 33° C. gave a pH of 5.33.

The solution prepared first, and stirred overnight, was pumped using a peristaltic pump (WATSON MARLOW 323E/D), into the freshly prepared solution with the ammonium heptamolybdate. The pumping procedure took about 26 minutes. Then the resulting suspension was admixed with 1.88 kg of a 0.1% solution of Praestol 611BC (Ashland 004041281623233) and 0.19 kg of Syloid C809 (Grace Davison; batch: 1000214955). The pH of the resulting suspension was 1.26. The resulting solution was stirred for 3 hours, before being sprayed into a pulsation reactor from IBU-tec (model: PR-4). The temperature in the pulsation reactor was 500° C. and the residence time was in the range from 200 ms to 2 s.

The yield of the resulting inventive composite material following discharge from the pulsation reactor was 2.20 kg. The BET surface area of the composite material was 40 $m^2/g$. The pore volume of the composite material was 0.16 $cm^3/g$. The particle size distribution was as follows:

$d_{10} = 122$ μm
$d_{50} = 47$ μm
$d_{90} = 4.2$ μm

Example 2

Production of an Inventive Washcoat Suspension

In the first production step, 2. 20 g of Geniosil GF95 (Wacker GD18168) and 1.69 g of 1M potassium hydroxide solution are introduced into 200 ml of distilled $H_2O$. Then first 128.21 g of the composite material produced in example 1, 9.62 g of Coconit 300 (Mahlwerk Neubauer-Friedrich Geffers) and 3.21 g of Syloid C809 (Grace Davison; batch: 1000214955) are suspended in the distilled water/Geniosil/KOH mixture produced in the $1^{st}$ step.

This is followed by an Ultra-Turrax treatment at 8000 rpm for about 2.5 minutes (T50 from IKA).). After the Turrax treatment, the suspension is transferred, with a further 300 ml of distilled $H_2O$, into a glass beaker, and 28.28 g of Bindzil 2034 Di (N00210) are added. This is followed by brief stirring and then by addition of 25.64 g of the organic binder EP 16 (from Wacker).

Example 3

Production of an Inventive Coated Catalyst 200 g of steatite spheres measuring 4.5 mm (EXACER # N.27/11) are swirled with air in an Innojet Aircoater 025 to form a fluidized bed, the temperature of the process air being 90° C. Subsequently, at a nozzle pressure of 1.0 bar and at a spraying rate of 4 g/min per 200 g of support body for coating, the washcoat suspension produced according to example 2 was introduced by spraying.

After the end of the spraying operation, the fluidization by the process air is halted, and the coated support bodies are discharged from the coating apparatus and then calcined in a calcining oven first at 400° C. for 2 hours and then, subsequently, at 610° C. for 3 hours.

The shell thickness of the catalytically active coating was 761 μm and the weight fraction of the applied coating was 27.4%.

In the present specification, the shell thickness is determined using the so-called slide caliper. In this case, an electronic slide caliper is used to measure the diameter of 40 catalyst beads, the average is formed, and then the diameter of the pure support beads is subtracted.

Comparative Example 1

Production of a Solid Extrudate Catalyst

First of all a bismuth-molybdenum mixed oxide powder was produced as per example 2 of DE 10 2008 017 308.

400 g of bismuth-molybdenum mixed oxide powder are introduced together with 23-53 g. of Syloid C809 (Grace Davison 1000214955), 35.29 g of Zusoplast C 92 (ZSCHWIMMER & SCHWARZ Ch. 143048 001) and 11.76 g of corn starch (batch QF05012412) into an extruder (Herrman Linde extruder model: LKII2) and mixed dry for 5 minutes. Then 117.65 g of Ludox AS 40 (Grace Davison batch: 510311) are added. Water is then added until an extrudable mass is produced (250 ml, approximately 50 ml every 3 minutes). Following the addition of 200 ml of water, compounding takes place for 15 minutes, and a further 50 ml are added in portions. Then 14.12 g g of steatite oil (Freidling from PA 10.12.10) are added, and compounding continues for 5 minutes more. (total compounding time: 40 min).

The compounded material thus obtained is introduced gradually into an ECT extruder. Die: 6 mm extrudates, 3 hole die; settings: drive screw: 30 rpm; pressure 7 to 8 bar.

The extrudates obtained are then dried in a VENTI-Line drying cabinet at 120° C. for one day. The dried extrudates are then calcined in a Nabertherm forced air oven at 590° C. for 8 hours. Calcining produces a weight loss of approximately 11% in the extrudates.

Comparative Example 2

Production of a Noninventive Coated Catalyst

First of all a composite material was produced as per example 1, with the difference that no pore formers were used for this purpose and the calcination was carried out in a calcining oven rather than in an IBU-tec pulsation reactor.

In accordance with example 2, a washcoat suspension was produced from the composite material produced accordingly, with the difference that, here again, no pore formers were added.

The resulting washcoat suspension was used to produce a coated catalyst in the same way as for example 3.

Comparative Example 3

First of all, a composite material was produced as per example 1, with the difference that no pore formers were used for this purpose. In accordance with example 2, a washcoat suspension was produced from the composite material produced accordingly, with the difference that, here again, no pore formers were added.

The resulting washcoat suspension was used to produce a coated catalyst in the same way as for example 3.

Catalytic Tests

The inventive coated catalyst of example 3 and the solid extrudate catalyst of comparative examples 1 to 3 were investigated for their catalytic performance in the conversion of propene to acrolein and acrylic acid. The feed composition here was 8.0 vol % water, 9.0% propene and 14.4% oxygen, the remainder being inert gas. The total flow rate in this case was 78 ml/min for each tube of the catalyst apparatus.

The catalytic performances of the inventive coated catalyst and of the solid extrudate catalyst are apparent from FIGS. 1 to 3. The catalytic performances of the inventive coated catalyst and of the catalyst of comparative example 2 are evident from FIGS. 4 to 6. The catalytic performances of the inventive coated catalyst and of the catalyst of comparative example 3 are evident from FIGS. 7 to 9.

The invention claimed is:

1. A composite material containing bismuth-molybdenum-nickel mixed oxide or bismuth-molybdenum-cobalt mixed oxide and $SiO_2$, the $SiO_2$ having a pore volume in the range from 0.1 to 10 ml/g and an average particle size in the range from 3 to 20 μm.

2. The composite material according to claim 1, wherein the composite material is a spray-calcined product of a spray composition comprising particulate porous $SiO_2$ having a pore volume in the range from 0.1 to 10 mL/g and an average particle size in the range from 3 to 20 μm; and salts of nickel, bismuth and molybdenum.

3. The composite material according to claim 2, wherein the spray-calcined product is made by spray-calcining the spray composition at a temperature in the range of 200–600° C.

4. The composite material according to claim 1, wherein the composite material is a spray-calcined product of a spray composition comprising particulate porous $SiO_2$ having a pore volume in the range from 0.1 to 10 mL/g and an average particle size in the range from 3 to 20 μm; and precipitated salts of nickel, bismuth and molybdenum.

5. The composite material according to claim 4, wherein the spray-calcined product is made by spray-calcining the spray composition at a temperature in the range of 200–600° C.

6. The composite material according to claim 1, wherein the composite material is made by a method comprising:
   (a) preparing a first aqueous solution containing salts of bismuth and of nickel;
   (b) preparing a second aqueous solution containing a molybdenum compound;
   (c) adding the first aqueous solution to the second aqueous solution, forming a first suspension;
   (d) adding a second suspension to the first suspension to form a third suspension, the second suspension containing $SiO_2$ which has a pore volume in the range from 0.1 to 10 ml/g and an average particle size in the range from 3 to 20 μm; and
   (e) spray-calcining the third suspension at a temperature in the range from 200 to 600° C., to give the composite material containing a bismuth-molybdenum-nickel mixed oxide or bismuth-molybdenum-cobalt mixed oxide.

7. The composite material according to claim 1, wherein the particulate porous $SiO_2$ has a pore volume in the range of 0.5 to 5 mL/g.

8. The composite material according to claim 1, wherein the particulate porous $SiO_2$ has a pore volume in the range of 1 to 2 mL/g.

9. The composite material according to claim 1, wherein the particulate porous $SiO_2$ has an average particle size in the range of 5 to 15 μm.

10. The composite material according to claim 1, wherein the particulate porous $SiO_2$ has an average particle size in the range of 8 to 11 μm.

11. The composite material according to claim 1, wherein the particulate porous $SiO_2$ an oil absorption value in the range of from 250 g/100 g to 400 g/100 g.

12. The composite material according to claim 1, having a BET surface area in the range of 20 to 60 $m^2/g$.

13. The composite material according to claim 1, having a pore volume in the range of 0.08 to 0.24 $cm^3/g$.

14. The composite material according to claim 1, having a pore volume in the range of 0.12 to 0.20 $cm^3/g$.

15. The composite material according to claim 1, wherein particles of the composite material have a $d_{90}$ particle size of less than 125 μm, a $d_{50}$ particle size less than 50 μm, and a $d_{10}$ particle size less than 7 μm.

* * * * *